United States Patent
Kadow et al.

(10) Patent No.: US 10,577,353 B2
(45) Date of Patent: *Mar. 3, 2020

(54) 5-(N-[6,5]-FUSED BICYCLIC ARYL TETRAHYDROISOQUINOLIN-6-YL) PYRIDIN-3-YL ACETIC ACID DERIVATIVES AS INHIBITORS OF HUMAN IMMUNODEFICIENCY VIRUS REPLICATION

(71) Applicant: ViiV Healthcare UK (No.5) Limited, Brentford, Middlesex (GB)

(72) Inventors: John F. Kadow, Wallingford, CT (US); B. Narasimhulu Naidu, Wallingford, CT (US); Tao Wang, Wallingford, CT (US); Zhiwei Yin, Wallingford, CT (US); Zhongxing Zhang, Wallingford, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/749,144

(22) PCT Filed: Aug. 10, 2016

(86) PCT No.: PCT/IB2016/054831
§ 371 (c)(1),
(2) Date: Jan. 31, 2018

(87) PCT Pub. No.: WO2017/025916
PCT Pub. Date: Feb. 16, 2017

(65) Prior Publication Data
US 2018/0222890 A1    Aug. 9, 2018

Related U.S. Application Data

(60) Provisional application No. 62/203,986, filed on Aug. 12, 2015.

(51) Int. Cl.
| | | |
|---|---|---|
| C07D 401/14 | (2006.01) |
| C07D 403/14 | (2006.01) |
| C07D 473/16 | (2006.01) |
| C07D 471/04 | (2006.01) |
| C07D 513/04 | (2006.01) |
| C07D 487/04 | (2006.01) |
| C07D 495/04 | (2006.01) |
| C07D 417/14 | (2006.01) |
| C07D 473/18 | (2006.01) |
| A61K 31/4427 | (2006.01) |
| A61P 31/18 | (2006.01) |
| A61K 31/5365 | (2006.01) |

(52) U.S. Cl.
CPC ........ *C07D 403/14* (2013.01); *A61K 31/4427* (2013.01); *A61P 31/18* (2018.01); *C07D 401/14* (2013.01); *C07D 417/14* (2013.01); *C07D 471/04* (2013.01); *C07D 473/16* (2013.01); *C07D 473/18* (2013.01); *C07D 487/04* (2013.01); *C07D 495/04* (2013.01); *C07D 513/04* (2013.01); *A61K 31/5365* (2013.01); *A61K 2300/00* (2013.01)

(58) Field of Classification Search
CPC .................................................. C07D 401/14
See application file for complete search history.

(56) References Cited

U.S. PATENT DOCUMENTS

2018/0230124 A1 * 8/2018 Eastman .............. C07D 401/14

FOREIGN PATENT DOCUMENTS

| EP | 2 719 685 A1 | 4/2014 |
| WO | WO 2010/130034 A1 | 11/2010 |
| WO | WO 2013/134113 A1 | 9/2013 |

* cited by examiner

*Primary Examiner* — Brian E McDowell
(74) *Attorney, Agent, or Firm* — Robert H. Brink; Kathryn A. Lutomski; Edward R. Gimmi

(57) ABSTRACT

Disclosed are compounds of Formula I, including pharmaceutically acceptable salts, pharmaceutical compositions comprising the compounds, methods for making the compounds and their use in inhibiting HIV integrase and treating those infected with HIV or AIDS.

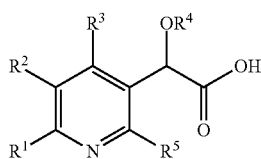

3 Claims, No Drawings

5-(N-[6,5]-FUSED BICYCLIC ARYL TETRAHYDROISOQUINOLIN-6-YL) PYRIDIN-3-YL ACETIC ACID DERIVATIVES AS INHIBITORS OF HUMAN IMMUNODEFICIENCY VIRUS REPLICATION

CROSS REFERENCE TO RELATED INVENTION

This application is a § 371 of International Application No. PCT/IB2016/054831, filed 10 Aug. 2016, which claims the benefit of U.S. Provisional Application No. 62/203,986, filed 12 Aug. 2015.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that an estimated 35.3 million people worldwide are infected with the virus (UNAIDS: Report on the Global HIV/AIDS Epidemic, 2013). In addition to the large number of individuals already infected, the virus continues to spread. Estimates from 2013 point to close to 3.4 million new infections in that year alone. In the same year there were approximately 1.6 million deaths associated with HIV and AIDS.

Current therapy for HIV-infected individuals consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity, i.e., cobicistat, available from Gilead Sciences, Inc. under the tradename TYBOST™ (cobicistat) tablets, has recently been approved for use in combinations with certain antiretroviral agents (ARVs) that may benefit from boosting.

In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See, for example, the following patent applications: WO2007131350, WO2009062285, WO2009062288, WO2009062289, WO2009062308, WO2010130034, WO2010130842, WO2011015641, WO2011076765, WO2012033735, WO2013123148, WO2013134113, WO2014164467, WO2014159959, and WO2015126726.

What is now needed in the art are additional compounds which are novel and useful in the treatment of HIV. Additionally, these compounds may desireably provide advantages for pharmaceutical uses, for example, with regard to one or more of their mechanisms of action, binding, inhibition efficacy, target selectivity, solubility, safety profiles, or bioavailability. Also needed are new formulations and methods of treatment which utilize these compounds.

SUMMARY OF THE INVENTION

The invention encompasses compounds of Formula I, including pharmaceutically acceptable salts thereof, as well as pharmaceutical compositions, and their use in inhibiting HIV and treating those infected with HIV or AIDS.

By virtue of the present invention, it is now possible to provide compounds that are novel and are useful in the treatment of HIV. Additionally, the compounds may provide advantages for pharmaceutical uses, for example, with regard to one or more of their mechanism of action, binding, inhibition efficacy, target selectivity, solubility, safety profiles, or bioavailability.

The invention also provides pharmaceutical compositions comprising the compounds of the invention, including pharmaceutically acceptable salts thereof, and a pharmaceutically acceptable carrier, excipient, and/or diluent.

In addition, the invention provides methods of treating HIV infection comprising administering a therapeutically effective amount of the compounds of the invention to a patient.

In addition, the invention provides methods for inhibiting HIV integrase.

Also provided in accordance with the invention are methods for making the compounds of the invention.

The present invention is directed to these, as well as other important ends, hereinafter described.

DESCRIPTION OF THE INVENTION

Unless specified otherwise, these terms have the following meanings.

"Alkyl" means a straight or branched saturated hydrocarbon comprised of 1 to 10 carbons, and preferably 1 to 6 carbons.

"Alkenyl" means a straight or branched alkyl group comprised of 2 to 10 carbons with at least one double bond and optionally substituted with 0-3 halo or alkoxy group.

"Alkynyl" means a straight or branched alkyl group comprised of 2 to 10 carbons, preferably 2 to 6 carbons, containing at least one triple bond and optionally substituted with 0-3 halo or alkoxy group.

"Aryl" mean a carbocyclic group comprised of 1-3 rings that are fused and/or bonded and at least one or a combination of which is aromatic. The non-aromatic carbocyclic portion, where present, will be comprised of $C_3$ to $C_7$ alkyl group. Examples of aromatic groups include, but are not limited to, indanyl, indenyl, naphthyl, phenyl, tetrahydronaphthyl and cyclopropylphenyl. The aryl group can be attached to the parent structure through any substitutable carbon atom in the group.

"Arylalkyl" is a $C_1$-$C_5$ alkyl group attached to 1 to 2 aryl groups and linked to the parent structure through the alkyl moiety. Examples include, but are not limited to, —$(CH_2)_n$Ph with n=1-5, —$CH(CH_3)$Ph, —$CH(Ph)_2$.

"Aryloxy" is an aryl group attached to the parent structure by oxygen.

"Cycloalkyl" means a monocyclic ring system composed of 3 to 7 carbons.

"Halo" includes fluoro, chloro, bromo, and iodo.

"Haloalkyl" and "haloalkoxy" include all halogenated isomers from monohalo to perhalo.

"Heteroaryl" is a subset of heterocyclic group as defined below and is comprised of 1-3 rings where at least one or a combination of which is aromatic and that the aromatic group contains at least one atom chosen from a group of oxygen, nitrogen or sulfur.

"Heterocyclyl or heterocyclic" means a cyclic group of 1-3 rings comprised of carbon and at least one other atom selected independently from oxygen, nitrogen and sulfur. The rings could be bridged, fused and/or bonded, through a direct or spiro attachment, with the option to have one or a combination thereof be aromatic. Examples include, but are not limited to, azaindole, azaindoline, azetidine, benzimidazole, bezodioxolyl, benzoisothiazole, benzothiazole, benzothiadiazole, benzothiophene, benzoxazole, carbazole, chroman, dihalobezodioxolyl, dihydrobenzofuran, dihydrobenzo[1,4]oxazine, 1,3-dihydrobenzo[c]thiophene 2,2-dioxide, 2,3-dihydrobenzo[d]isothiazole 1,1-dioxide, 3,4-dihydro-2H-pyrido[3,2-b][1,4]oxazine, 2,3-dihydro-1H-pyrrolo[3,4-c]pyridine and its regioisomeric variants, 6,7-dihydro-5H-pyrrolo[2,3-b]pyrazine and its regioisomeric variants, furanylphenyl, imidazole, imidazo[1,2-a]pyridine, indazole, indole, indoline, isoquinoline, isoquinolinone, isothiazolidine 1,1-dioxide, morpholine, 2-oxa-5-azabicyclo[2.2.1]heptane, oxadiazole-phenyl, oxazole, phenylaztidine, phenylindazole, phenylpiperidine, phenylpiperizine, phenyloxazole, phenylpyrrolidine, piperidine, pyridine, pyridinylphenyl, pyridinylpyrrolidine, pyrimidine, pyrimidinylphenyl, pyrrazole-phenyl, pyrrolidine, pyrrolidin-2-one, 1H-pyrazolo[4,3-c]pyridine and its regioisomeric variants, pyrrole, 5H-pyrrolo[2,3-b]pyrazine, 7H-pyrrolo[2,3-d]pyrimidine and its regioisomeric variants, quinazoline, quinoline, quinoxaline, tetrahydroisoquinoline, 1,2,3,4-tetrahydro-1,8-naphthyridine, tetrahydroquinoline, 4,5,6,7-tetrahydrothieno[3,2-c]pyridine, 1,2,5-thiadiazolidine 1,1-dioxide, thiophene, thiophenylphenyl, triazole, or triazolone. Unless otherwise specifically set forth, the heterocyclic group can be attached to the parent structure through any suitable atom in the group that results in a stable compound.

It is understood that a subset of the noted heterocyclic examples encompass regioisomers. For instance, "azaindole" refers to any of the following regioisomers: 1H-pyrrolo[2,3-b]pyridine, 1H-pyrrolo[2,3-c]pyridine, 1H-pyrrolo[3,2-c]pyridine, and 1H-pyrrolo[3,2-b]pyridine. In addition the "regioisomer variants" notation as in, for example, "5H-pyrrolo[2,3-b]pyrazine and its regioisomeric variants" would also encompass 7H-pyrrolo[2,3-d]pyrimidine, 7H-pyrrolo[2,3-c]pyridazine, 1H-pyrrolo[2,3-d]pyridazine, 5H-pyrrolo[3,2-c]pyridazine, and 5H-pyrrolo[3,2-d]pyrimidine. Similarly, 6,7-dihydro-5H-pyrrolo[2,3-b]pyrazine and its regioisomeric variants would encompass 6,7-dihydro-5H-pyrrolo[2,3-d]pyrimidine and 6,7-dihydro-5H-pyrrolo[2,3-c]pyridazine. It is also understood that the lack of "regioisomeric variants" notation does not in any way restrict the claim scope to the noted example only.

"Heterocyclylalkyl" is a heterocyclyl moiety attached to the parent structure through $C_1$-$C_5$ alkyl group. Examples include, but are not limited to, —$(CH_2)_n$—$R^Z$ or —CH$(CH_3)$—$(R^Z)$ where n=1-5 and that $R^Z$ is chosen from benzimidazole, imidazole, indazole, isooxazole, phenylpyrazole, pyridine, quinoline, thiazole, triazole, triazolone, oxadiazole.

Terms with a hydrocarbon moiety (e.g. alkoxy) include straight and branched isomers for the hydrocarbon portion with the indicated number of carbon atoms.

Bonding and positional bonding relationships are those that are stable as understood by practitioners of organic chemistry.

Parenthetic and multiparenthetic terms are intended to clarify bonding relationships to those skilled in the art. For example, a term such as ((R)alkyl) means an alkyl substituent further substituted with the substituent R.

Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

"Combination," "coadministration," "concurrent" and similar terms referring to the administration of a compound of Formula I with at least one anti-HIV agent mean that the components are part of a combination antiretroviral therapy or highly active antiretroviral therapy ("HAART") as understood by practitioners in the field of AIDS and HIV infection.

"Therapeutically effective" means the amount of agent required to provide a benefit to a patient as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus.

"Treatment," "therapy," "regimen," "HIV infection," "ARC," "AIDS" and related terms are used as understood by practitioners in the field of AIDS and HIV infection.

Those terms not specifically set forth herein shall have the meaning which is commonly understood and accepted in the art.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

In an aspect of the invention, there is provided a compound of Formula I:

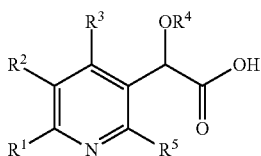

wherein:
$R^1$ is selected from hydrogen, alkyl, or cycloalkyl;
$R^2$ is tetrahydroisoquinolinyl and is substituted with 1 $R^6$ substituent and also with 0-3 halo or alkyl substituents;
$R^3$ is selected from azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, alkoxy, and haloalkoxy;
$R^4$ is selected from alkyl or haloalkyl;
$R^5$ is alkyl; and
$R^6$ is selected from benzothiazolyl, pyrazolopyrimidinyl, thiazolopyridinyl, triazolopymidinyl, benzooxazolyl, pyrrolopyrimidinyl, purinyl, imidazopyridinyl, benzoisoxazolyl, benzoimidazolyl or thienopyrimidinyl, and is substituted with 0-3 substituents selected from amino, cyano, halo, hydroxyl, alkyl, haloalkyl, alkoxy, and haloalkoxy;
or a pharmaceutically acceptable salt thereof.

In an aspect of the invention, $R^2$ is tetrahydroisoquinolinyl substituted with 1 $R^6$ substituent.

In an aspect of the invention, $R^3$ is piperidinyl substituted with 0-3 substituents selected from cyano, halo, alkyl, haloalkyl, alkoxy, and haloalkoxy.

In an aspect of the invention, there is provided a compound of Formula I:

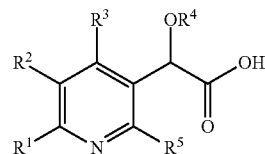

wherein:
$R^1$ is selected from hydrogen, alkyl, or cycloalkyl;
$R^2$ is tetrahydroisoquinolinyl and is substituted with 1 $R^6$ substituent;
$R^3$ is selected from azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, alkoxy, and haloalkoxy;
$R^4$ is selected from alkyl or haloalkyl;
$R^5$ is alkyl; and
$R^6$ is selected from benzothiazolyl, pyrazolopyrimidinyl, thiazolopyridinyl, triazolopymidinyl, benzooxazolyl, pyrrolopyrimidinyl, purinyl, imidazopyridinyl, benzoisoxazolyl, benzoimidazolyl or thienopyrimidinyl, and is substituted with 0-3 substituents selected from amino, cyano, halo, hydroxyl, alkyl, haloalkyl, alkoxy, and haloalkoxy;
or a pharmaceutically acceptable salt thereof.

In an aspect of the invention, there is provided a compound of Formula I:

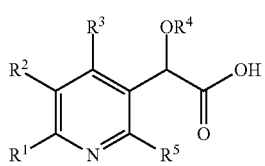

wherein:
$R^1$ is selected from hydrogen, alkyl, or cycloalkyl;
$R^2$ is tetrahydroisoquinolinyl and is substituted with 1 $R^6$ substituent and also with 0-3 halo or alkyl substituents;
$R^3$ is piperidinyl substituted with 0-3 substituents selected from cyano, halo, alkyl, haloalkyl, alkoxy, and haloalkoxy;
$R^4$ is selected from alkyl or haloalkyl;
$R^5$ is alkyl; and
$R^6$ is selected from benzothiazolyl, pyrazolopyrimidinyl, thiazolopyridinyl, triazolopymidinyl, benzooxazolyl, pyrrolopyrimidinyl, purinyl, imidazopyridinyl, benzoisoxazolyl, benzoimidazolyl or thienopyrimidinyl, and is substituted with 0-3 substituents selected from amino, cyano, halo, hydroxyl, alkyl, haloalkyl, alkoxy, and haloalkoxy;
or a pharmaceutically acceptable salt thereof.

For a particular compound of Formula I, the scope of any instance of a variable substituent, including $R^1$, $R^2$, $R^3$, $R^4$, $R^5$ and $R^6$ can be used independently with the scope of any other instance of a variable substituent. As such, the invention includes combinations of the different aspects.

In an aspect of the invention, there is provided a composition useful for treating HIV infection comprising a therapeutic amount of a compound of Formula I and a pharmaceutically acceptable carrier. In an aspect of the invention, the composition further comprises a therapeutically effective amount at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier. In an aspect of the invention, the other agent is dolutegravir.

In an aspect of the invention, there is provided a method for treating HIV infection comprising administering a therapeutically effective amount of a compound of Formula I, or a pharmaceutically acceptable salt thereof, to a patient in need thereof. In an aspect of the invention, the method further comprises administering a therapeutically effective amount of at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors. In an aspect of the invention, the other agent is dolutegravir.

In an aspect of the invention, the other agent is administered to the patient prior to, simultaneously with, or subsequently to the compound of Formula I.

Preferred compounds in accordance with the present invention include the following:

(S)-2-(tert-butoxy)-2-(4-(4,4-dimethylpiperidin-1-yl)-2,6-dimethyl-5-(2-(6-(trifluoromethyl)thiazolo[4,5-b]pyridin-2-yl)-1,2,3,4-tetrahydroisoquinolin-6-yl)pyridin-3-yl)acetic acid;

(S)-2-(tert-butoxy)-2-(4-(4,4-dimethylpiperidin-1-yl)-2,6-dimethyl-5-(2-(thiazolo[5,4-b]pyridin-2-yl)-1,2,3,4-tetrahydroisoquinolin-6-yl)pyridin-3-yl)acetic acid;

(S)-2-(tert-butoxy)-2-(5-(2-(7-chlorothiazolo[5,4-c]pyridin-2-yl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(6-chlorobenzo[d]thiazol-2-yl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(5,6-dichlorobenzo[d]thiazol-2-yl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-2,6-dimethyl-5-(2-(5-methylbenzo[d]thiazol-2-yl)-1,2,3,4-tetrahydroisoquinolin-6-yl)pyridin-3-yl)acetic acid;

(S)-2-(tert-butoxy)-2-(5-(2-(4-chlorobenzo[d]thiazol-2-yl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(6-fluorobenzo[d]thiazol-2-yl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-2,6-dimethyl-5-(2-(6-methylbenzo[d]thiazol-2-yl)-1,2,3,4-tetrahydroisoquinolin-6-yl)pyridin-3-yl)acetic acid;

(S)-2-(tert-butoxy)-2-(4-(4,4-dimethylpiperidin-1-yl)-2,6-dimethyl-5-(2-(thiazolo[4,5-b]pyridin-2-yl)-1,2,3,4-tetrahydroisoquinolin-6-yl)pyridin-3-yl)acetic acid;

(S)-2-(tert-butoxy)-2-(4-(4,4-dimethylpiperidin-1-yl)-2,6-dimethyl-5-(2-(thiazolo[4,5-c]pyridin-2-yl)-1,2,3,4-tetrahydroisoquinolin-6-yl)pyridin-3-yl)acetic acid;

(S)-2-(tert-butoxy)-2-(4-(4,4-dimethylpiperidin-1-yl)-5-(2-(6-methoxybenzo[d]thiazol-2-yl)-1,2,3,4-tetrahydroisoquinolin-6-yl)-2,6-dimethylpyridin-3-yl)acetic acid;

(S)-2-(5-(2-(benzo[d]thiazol-2-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid;

(S)-2-(tert-butoxy)-2-(4-(4,4-dimethylpiperidin-1-yl)-2,6-dimethyl-5-(2-(thieno[2,3-d]pyrimidin-4-yl)-1,2,3,4-tetrahydroisoquinolin-6-yl)pyridin-3-yl)acetic acid;

(S)-2-(tert-butoxy)-2-(4-(4,4-dimethylpiperidin-1-yl)-2,6-dimethyl-5-(2-(7-methylthieno[3,2-d]pyrimidin-4-yl)-1,2,3,4-tetrahydroisoquinolin-6-yl)pyridin-3-yl)acetic acid; and (S)-2-(tert-butoxy)-2-(4-(4,4-dimethylpiperidin-1-yl)-2,6-dimethyl-5-(2-(1-methyl-1H-pyrazolo[3,4-d]pyrimidin-4-yl)-1,2,3,4-tetrahydroisoquinolin-6-yl)pyridin-3-yl)acetic acid;

(S)-2-(tert-butoxy)-2-(4-(4,4-dimethylpiperidin-1-yl)-2,6-dimethyl-5-(2-(1-methyl-1H-benzo[d]imidazol-2-yl)-1,2,3,4-tetrahydroisoquinolin-6-yl)pyridin-3-yl)acetic acid;

(S)-2-(5-(2-(benzo[d]isoxazol-3-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid;

(S)-2-(tert-butoxy)-2-(5-(2-(1,6-dimethyl-1H-pyrazolo[3,4-d]pyrimidin-4-yl)-1,2,3,4-tetrahydroisoquinolin-6-yl)-4-(4,4-dimethylpiperidin-1-yl)-2,6-dimethylpyridin-3-yl)acetic acid;

(S)-2-(5-(2-(7H-pyrrolo[2,3-d]pyrimidin-4-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid;

(S)-2-(tert-butoxy)-2-(4-(4,4-dimethylpiperidin-1-yl)-5-(2-(6-hydroxy-7H-purin-2-yl)-1,2,3,4-tetrahydroisoquinolin-6-yl)-2,6-dimethylpyridin-3-yl)acetic acid;

(S)-2-(5-(2-(5H-pyrrolo[3,2-d]pyrimidin-4-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid;

(S)-2-(tert-butoxy)-2-(4-(4,4-dimethylpiperidin-1-yl)-2,6-dimethyl-5-(2-(6-(methylamino)-7H-purin-2-yl)-1,2,3,4-tetrahydroisoquinolin-6-yl)pyridin-3-yl)acetic acid;

(S)-2-(5-(2-(1H-imidazo[4,5-c]pyridin-4-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid;

(S)-2-(5-(2-(7H-pyrrolo[2,3-d]pyrimidin-2-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid;

(S)-2-(5-(2-(7H-purin-6-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid;

(S)-2-(tert-butoxy)-2-(4-(4,4-dimethylpiperidin-1-yl)-5-(2-(2-methoxy-7H-pyrrolo[2,3-d]pyrimidin-4-yl)-1,2,3,4-tetrahydroisoquinolin-6-yl)-2,6-dimethylpyridin-3-yl) acetic acid;

(S)-2-(tert-butoxy)-2-(5-(2-(6-(tert-butyl)thieno[3,2-d]pyrimidin-4-yl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(5-chlorobenzo[d]oxazol-2-yl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-2,6-dimethyl-5-(2-(3-phenyl-3H-[1,2,3]triazolo[4,5-d]pyrimidin-7-yl)-1,2,3,4-tetrahydroisoquinolin-6-yl)pyridin-3-yl)acetic acid; and pharmaceutically acceptable salts thereof.

The compounds of the invention herein described may typically be administered as pharmaceutical compositions. These compositions are comprised of a therapeutically effective amount of a compound of Formula I or its pharmaceutically acceptable salt, and a pharmaceutically acceptable carrier and may contain conventional excipients and/or diluents. A therapeutically effective amount is that which is needed to provide a meaningful patient benefit. Pharmaceutically acceptable carriers are those conventionally known carriers having acceptable safety profiles. Compositions encompass all common solid and liquid forms, including capsules, tablets, lozenges, and powders, as well as liquid suspensions, syrups, elixirs, and solutions. Compositions are made using available formulation techniques, and excipients (such as binding and wetting agents) and vehicles (such as water and alcohols) which are generally used for compositions. See, for example, Remington's Pharmaceutical Sciences, 17th edition, Mack Publishing Company, Easton, Pa. (1985).

Solid compositions which are normally formulated in dosage units and compositions providing from about 1 to 1000 milligram ("mg") of the active ingredient per dose are typical. Some examples of dosages are 1 mg, 10 mg, 100 mg, 250 mg, 500 mg, and 1000 mg. Generally, other antiretroviral agents will be present in a unit range similar to agents of that class used clinically. Typically, this is about 0.25-1000 mg/unit.

Liquid compositions are usually in dosage unit ranges. Generally, the liquid composition will be in a unit dosage range of about 1-100 milligram per milliliter ("mg/mL"). Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is about 1-100 mg/mL.

The invention encompasses all conventional modes of administration; oral and parenteral methods are preferred. Generally, the dosing regimen will be similar to other antiretroviral agents used clinically. Typically, the daily dose will be about 1-100 milligram per kilogram ("mg/kg") body weight daily. Generally, more compound is required orally and less parenterally. The specific dosing regimen, however, will be determined by a physician using sound medical judgment.

The compounds of this invention desireably have activity against HIV. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier, excipient and/or diluent.

The invention also encompasses methods where the compound is given in combination therapy. That is, the compound can be used in conjunction with, but separately from, other agents useful in treating AIDS and HIV infection. The compound can also be used in combination therapy wherein the compound and one or more of the other agents are physically together in a fixed-dose combination (FDC). Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, HIV capsid inhibitors, anti-infectives, and immunomodulators, such as, for example, PD-1 inhibitors, PD-L1 inhibitors, antibodies, and the like. In these combination methods, the compound of Formula I will generally be given in a daily dose of about 1-100 mg/kg body weight daily in conjunction with other agents. The other agents generally will be given in the amounts used therapeutically. The specific dosing regimen, however, will be determined by a physician using sound medical judgment.

Examples of nucleoside HIV reverse transcriptase inhibitors include abacavir, didanosine, emtricitabine, lamivudine, stavudine, tenofovir, zalcitabine, and zidovudine.

Examples of non-nucleoside HIV reverse transcriptase inhibitors include delavirdine, efavirenz, etrivirine, nevirapine, and rilpivirine.

Examples of HIV protease inhibitors include amprenavir, atazanavir, darunavir, fosamprenavir, indinavir, lopinavir, nelfinavir, ritonavir, saquinavir and, tipranavir.

An example of an HIV fusion inhibitor is enfuvirtide or T-1249.

An example of an HIV entry inhibitor is maraviroc.

Examples of HIV integrase inhibitors include dolutegravir, elvitegravir, or raltegravir.

An example of an HIV attachment inhibitor is fostemsavir.

An example of an HIV maturation inhibitor is BMS-955176, having the following structure:

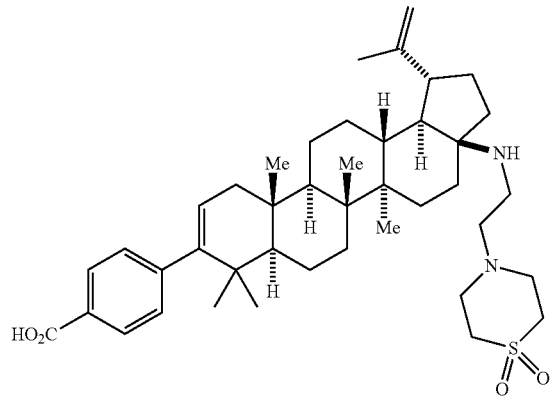

Thus, as set forth above, contemplated herein are combinations of the compounds of Formula I, together with one or more agents useful in the treatment of AIDS. For example, the compounds of the invention may be effectively administered, whether at periods of pre-exposure and/or post-exposure, in combination with effective amounts of the AIDS antivirals, immunomodulators, anti-infectives, or vaccines, such as those in the following non-limiting table:

| Drug Name | Manufacturer | Indication |
|---|---|---|
| ANTIVIRAL | | |
| Rilpivirine | Tibotec | HIV infection, AIDS, ARC (non-nucleoside reverse transcriptase inhibitor) |
| COMPLERA ® | Gilead | HIV infection, AIDS, ARC; combination with emtricitabine, rilpivirine, and tenofovir disoproxil fumarate |

-continued

| Drug Name | Manufacturer | Indication |
|---|---|---|
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |

-continued

| Drug Name | Manufacturer | Indication |
|---|---|---|
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |

-continued

| Drug Name | Manufacturer | Indication |
|---|---|---|
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ™ Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDS in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® | Oncolys BioPharma | HIV infection AIDs in development |
| CMX-157 Lipid conjugate of nucleotide tenofovir | Chimerix | HIV infection AIDs |
| GSK1349572 Integrase inhibitor TIVICAY ® dolutegravir | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |

-continued

| Drug Name | Manufacturer | Indication |
|---|---|---|
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |

| Drug Name | Manufacturer | Indication |
| --- | --- | --- |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Methods of Synthesis

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et₂O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Certain other abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds of this invention can be prepared by the methods outlined in the Scheme I

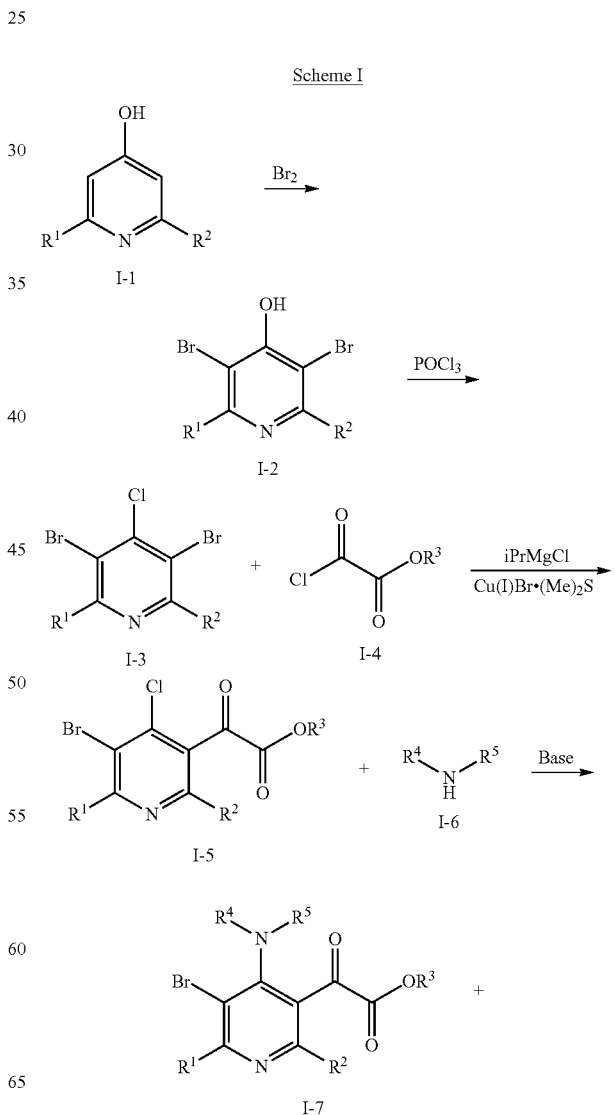

Scheme I

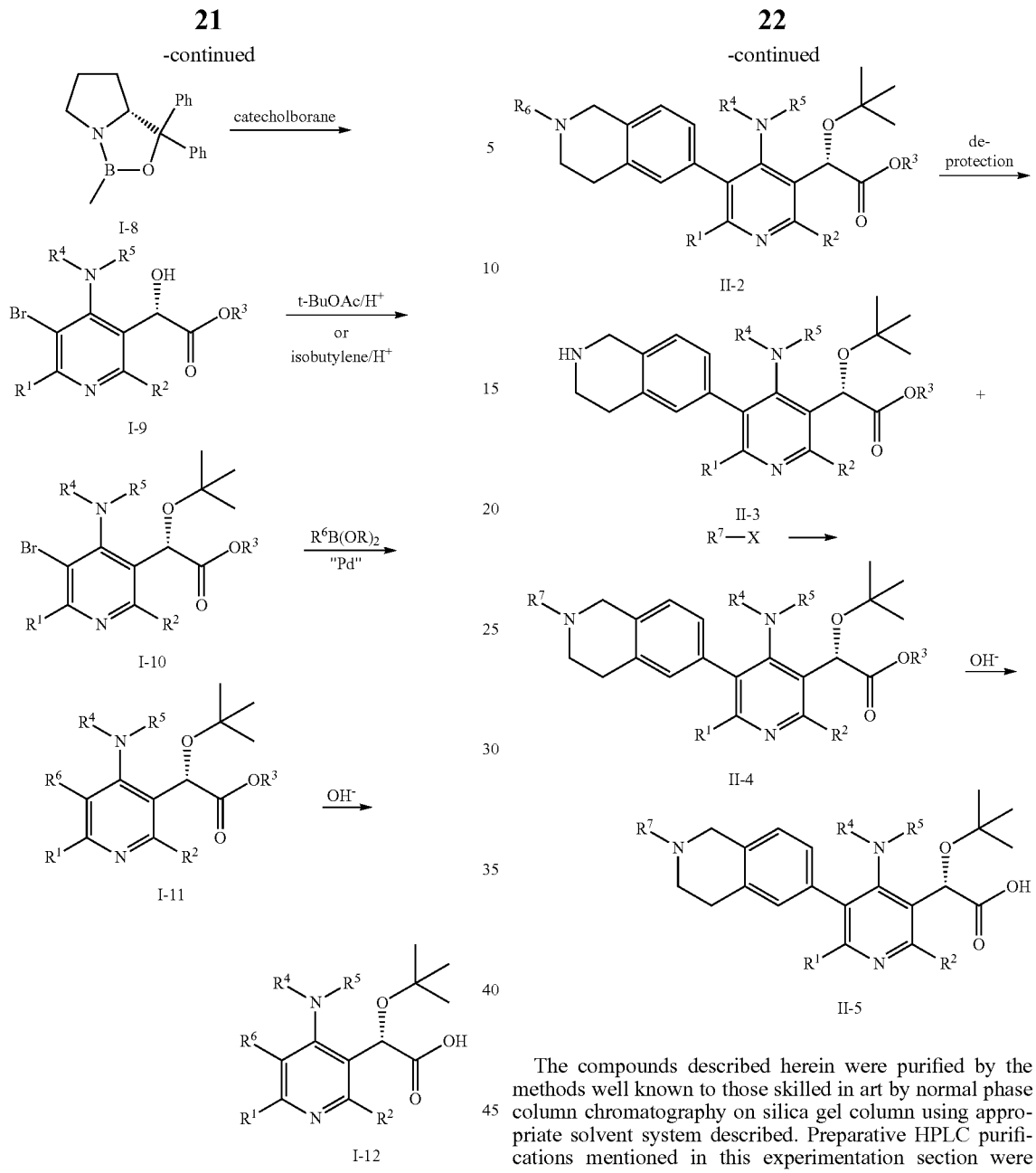

Some compounds of this invention can be prepared by the methods outlined in the Scheme II.

Scheme II

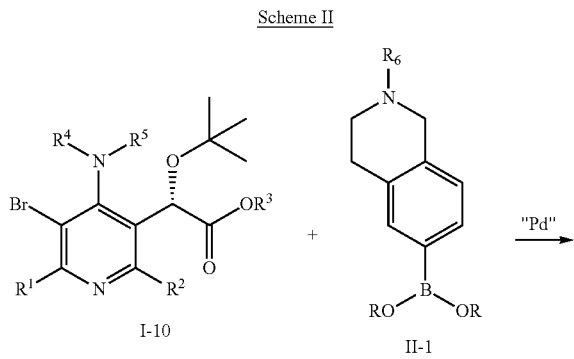

The compounds described herein were purified by the methods well known to those skilled in art by normal phase column chromatography on silica gel column using appropriate solvent system described. Preparative HPLC purifications mentioned in this experimentation section were carried out gradient elution either on Sunfire Prep C18 ODB column (5 μm; 19 or 30×100 mm) or Waters Xbridge C18 column (5 μM; 19×200 or 30×100 mm) or Water Atlantis (5 μm; 19 or 30×100 mm) using the following mobile phases. Mobile phase A: 9:1 $H_2O$/acetonitrile with 10 mM $NH_4OAc$ and mobile phase B:A: 9:1 acetonitrile/$H_2O$ with 10 mM $NH_4OAc$; or mobile phase A: 9:1 $H_2O$/acetonitrile with 0.1% TFA and mobile phase B:A: 9:1 acetonitrile/$H_2O$ with 0.1% TFA; or mobile phase A: water/MeOH (9:1) with 20 mM $NH_4OAc$ and mobile phase B: 95:5 MeOH/$H_2O$ with 20 mM $NH_4OAc$ or mobile phase A: water/MeOH (9:1) with 0.1% TFA and mobile phase B: 95:5 MeOH/$H_2O$ with 0.1% TFA or mobile Phase A: 5:95 acetonitrile:water with 10-mM ammonium acetate; Mobile Phase B: 95:5 acetonitrile:water with 10-mM ammonium acetate.

All Liquid Chromatography (LC) data were recorded on a Shimadzu LC-10AS or LC-20AS liquid chromotograph using a SPD-10AV or SPD-20A UV-Vis detector and Mass Spectrometry (MS) data were determined with a Micromass Platform for LC in electrospray mode.

Compounds purified by preparative HPLC were diluted in methanol (1.2 mL) and purified using a Shimadzu LC-8A or LC-10A automated preparative HPLC system.

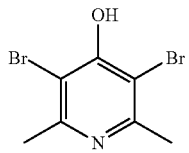

3,5-Dibromo-2,6-dimethylpyridin-4-ol

A 3-neck R.B-flask equipped with mechanical stirrer, addition funnel and condenser is charged with 2,6-dimethylpyridin-4-ol (100 g, 812 mmol), CH$_2$Cl$_2$ (1000 mL) and MeOH (120 mL). To the resulting light brown or tan solution was added tert-BuNH2 (176 ml, 1665 mmol), cooled in water bath maintained between 5-10° C. (ice-water) and added drop wise Br2 (84 ml, 1624 mmol) over 70 min. After the addition was complete cold bath was removed and stirred for 1.5 h at rt. Then, the light orange slurry was filtered and the filter cake was washed with ether (250 mL) and dried to afford 3,5-dibromo-2,6-dimethylpyridin-4-ol, hydrobromide (280.75 g, 776 mmol, 96% yield) as white solid which was used in the next step without further purification. $^1$H NMR (500 MHz, DMSO-d$_6$) δ 12.08 (br. s., 1H), 2.41 (s, 6H). LCMS (M+H)=281.9.

Alternative Procedure:

Bromine (72.8 mL, 1.4 mol) was added via addition funnel over 60 min to a mechanically stirred cold (ice-water bath) solution of 2,6-dimethylpyridin-4-ol (87 g, 706 mmol) and 4-methylmorpholine (156 mL, 1.4 mol) in dichloromethane (1 L) and methanol (100 mL) and then stirred for 2 h at rt. Additional bromine (~15 mL) was added based on monitoring by LCMS. The product was filtered, washed with ether, and dried under vacuum to give 3,5-dibromo-2,6-dimethylpyridin-4-ol 176.8 g (88%).

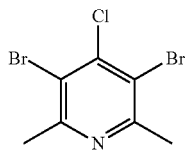

3,5-Dibromo-4-chloro-2,6-dimethylpyridine

Triethylamine (28.8 mL, 206 mmol) was added to a nitrogen purged solution of 3,5-dibromo-2,6-dimethylpyridin-4-ol (58 g, 206 mmol) and phosphorous oxychloride (57.7 mL, 619 mmol) in chloroform (450 mL) and stirred for 1 h at rt, then 3 h at 80° C. The reaction was removed from heating and immediately concentrated under house vacuum; then under high vacuum. The appearance was a cream colored solid, which was azeotroped with toluene (2×100 mL); treated with ice (200 g) for 10 min and carefully neutralized with NaHCO$_3$ (powder), and 1N NaOH solution, and extracted with DCM (2×400 mL). The combined organic layers were dried (MgSO$_4$), concentrated, and a beige solid was obtained that was washed with hexanes and dried under high vacuum to give 3,5-dibromo-4-chloro-2,6-dimethylpyridine 52.74 g (85.1%). Concentration of the hexanes gave 3.5 g of less pure product. $^1$H NMR (500 MHz, CDCl$_3$) δ 2.59 (s, 6H). LCMS (M+H)=300.0.

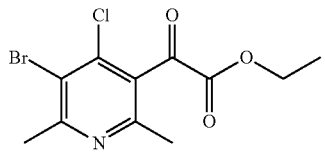 [SMILES: CCOC(=O)C(=O)c1c(C)nc(C)c(Br)c1Cl]

Ethyl 2-(5-bromo-4-chloro-2,6-dimethylpyridin-3-yl)-2-oxoacetate

To a stirred mixture of 3,5-dibromo-4-chloro-2,6-dimethylpyridine (14.94 g, 49.9 mmol) and Cu(I)Br Me2S (0.513 g, 2.495 mmol) in THF (50 mL) was added drop wise 2M iPrMgCl/THF (26.2 ml, 52.4 mmol) at −30° C. over 5 min. Then, the resulting slurry was warmed to −10° C. over 30 min and stirred for 30 min. The homogeneous brown reaction mixture was rapidly transferred via cannula to a solution of ethyl 2-chloro-2-oxoacetate (6.14 ml, 54.9 mmol, degassed for 5 min by bubbling N2 through the solution) in THF (50 mL) maintained at −30° C. The resulting reaction mixture was stirred (1.5 h) while warming to 0° C. Then, taken up in to Et$_2$O (200 mL), washed with 1:1 sat Na$_2$CO$_3$/1M NH$_4$Cl (3×50 mL), dried (MgSO$_4$), filtered and concentrated to give brown viscous oil. Flash chromatography using 2.5, 5 and 7.5% EtOAc/Hex afforded ethyl 2-(5-bromo-4-chloro-2,6-dimethylpyridin-3-yl)-2-oxoacetate (14.37 g, 44.8 mmol, 90% yield) as white solid. $^1$H NMR (400 MHz, CDCl$_3$) δ 4.42 (q, J=7.0 Hz, 2H), 2.76 (s, 3H), 2.46 (s, 3H), 1.41 (t, J=7.2 Hz, 3H). LCMS (M+H)=322.1.

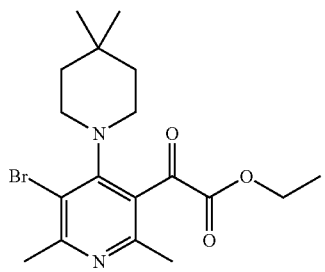 [SMILES: CCOC(=O)C(=O)c1c(C)nc(C)c(Br)c1N1CCC(C)(C)CC1]

Ethyl 2-(5-bromo-4-(4,4-dimethylpiperidin-1-yl)-2,6-dimethylpyridin-3-yl)-2-oxoacetate To a solution of 4,4-dimethylpiperidine (1.245 g, 11.00 mmol) and DIEA (3.49 ml, 20.00 mmol) in anhydrous CH$_3$CN (40 mL) was added ethyl 2-(5-bromo-4-chloro-2,6-dimethylpyridin-3-yl)-2-oxoacetate (3.21 g, 10 mmol) at rt. The resulting mixture was placed in a pre-heated oil bath (80° C.). After 22 h, the reaction mixture was concentrated and the residue was purified by flash chromatography using 1-lit each 2.5, 5, 7.5 and 10% EtOAc/Hex to afford ethyl 2-(5-bromo-4-(4,4-dimethylpiperidin-1-yl)-2,6-dimethylpyridin-3-yl)-2-oxoacetate (2.846 g, 7.16 mmol, 71.6% yield) as yellow solid. $^1$H NMR (500 MHz, CDCl$_3$) δ 4.37 (q, J=7.1 Hz, 2H), 3.67-2.75 (br.s., 4H), 2.71 (s, 3H), 2.44 (s, 3H), 1.42 (t, J=7.1 Hz, 3H), 1.38 (t, J=5.6 Hz, 4H), 1.00 (s, 6H). LCMS (M+H)=399.4.

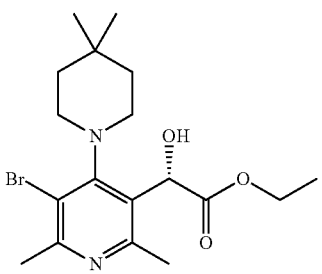 [SMILES: CCOC(=O)[C@@H](O)c1c(C)nc(C)c(Br)c1N1CCC(C)(C)CC1]

(S)-Ethyl 2-(5-bromo-4-(4,4-dimethylpiperidin-1-yl)-2,6-dimethylpyridin-3-yl)-2-hydroxyacetate To stirred yellow solution of ethyl 2-(5-bromo-4-(4,4-dimethylpiperidin-1-yl)-2,6-dimethylpyridin-3-yl)-2-oxoacetate (2.25 g, 5.66 mmol) and (R)-1-methyl-3,3-diphenyl-hexahydropyrrolo[1,2-c][1,3,2]oxazaborole (0.314 g, 1.133 mmol) in toluene (30 mL) at −35° C. was added drop wise 50% catecholborane (1.819 ml, 8.49 mmol) over 10 min. The reaction mixture was slowly warmed to −15° C. over 1 h and then left for 2 h at −15° C. Then, diluted with EtOAc (100 mL), washed with sat $Na_2CO_3$ (4×25 mL) by vigorously stirring and separating aqueous layers. The organic layer dried ($MgSO_4$), filtered, concentrated and purified by flash chromatography using 10, 20 and 25% EtOAc/Hex to afford desired (S)-ethyl 2-(5-bromo-4-(4,4-dimethylpiperidin-1-yl)-2,6-dimethylpyridin-3-yl)-2-hydroxyacetate (2.2596 g, 5.66 mmol, 100% yield) contaminated with about 10% of (S)-ethyl 2-(5-bromo-4-chloro-2,6-dimethylpyridin-3-yl)-2-hydroxyacetate. Used in the next step without further purification. $^1$H NMR (500 MHz, $CDCl_3$) δ 5.71 (d, J=7.3 Hz, 1H), 5.54 (d, J=7.4 Hz, 1H), 4.29 (dq, J=10.8, 7.1 Hz, 1H), 4.16 (dq, J=10.8, 7.1 Hz, 1H), 3.94-3.83 (m, 2H), 2.71 (d, J=11.9 Hz, 1H), 2.67 (s, 3H), 2.59 (s, 3H), 2.54 (d, J=12.0 Hz, 1H), 1.71 (td, J=12.7, 4.7 Hz, 1H), 1.62 (td, J=13.0, 4.7 Hz, 1H), 1.42 (dd, J=13.1, 2.2 Hz, 1H), 1.37 (dd, J=12.9, 2.4 Hz, 1H), 1.25 (t, J=7.1 Hz, 3H), 1.09 (s, 3H), 1.04 (s, 3H). LCMS (M+H)=401.3.

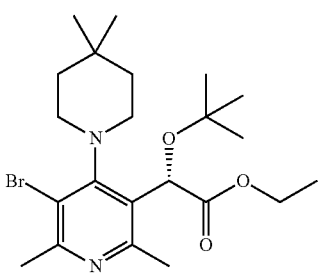 [SMILES: CCOC(=O)[C@@H](OC(C)(C)C)c1c(C)nc(C)c(Br)c1N1CCC(C)(C)CC1]

(S)-Ethyl 2-(5-bromo-4-(4,4-dimethylpiperidin-1-yl)-2,6-dimethylpyridin-3-yl)-2-(tert-butoxy)acetate A stirred ice-cold yellow mixture of (S)-ethyl 2-(5-bromo-4-(4,4-dimethylpiperidin-1-yl)-2,6-dimethylpyridin-3-yl)-2-hydroxyacetate (2.45 g, 6.14 mmol) and 70% $HClO_4$ (1.054 ml, 12.27 mmol) in $CH_2Cl_2$ (100 mL) was saturated with isobutylene gas by bubbling through the reaction mixture (10 min). After 2 h, cold bath was removed and the turbid reaction mixture stirred for 22 h at rt. LCMS at this point showed 4:1 product to sm. So, saturated with isobutylene (5 min) at rt and stirred for additional 24 h. Then, neutralized with sat. $Na_2CO_3$ (30 mL), organic layer separated and aqueous layer extracted with $CH_2Cl_2$ (25 mL). The combined organic layers dried ($MgSO_4$), filtered, concentrated and purified by flash chromatography using 5, 10, 15, 20 and 40% EtOAc/hex to afford (S)-ethyl 2-(5-bromo-4-(4,4-dimethylpiperidin-1-yl)-2,6-dimethylpyridin-3-yl)-2-(tert-butoxy)acetate (2.3074 g, 5.07 mmol, 83% yield) as yellow oil: $^1$H NMR (500 MHz, $CDCl_3$) δ 6.19 (br. s., 1H), 4.17-4.24 (m, 1H), 4.08-4.14 (m, 1H), 4.04 (dt, J=2.5, 12.1 Hz, 1H), 3.51 (dt, J=2.5, 12.1 Hz, 1H), 2.85-2.91 (m, 1H), 2.64 (s, 3H), 2.57-2.62 (m, 1H), 2.55 (s, 3H), 1.55-1.66 (m, 2H), 1.41-1.46 (m, 1H), 1.32-1.37 (m, 1H), 1.21 (s, 9H), 1.20 (t, J=7.2 Hz, 2H), 1.08 (s, 3H), 1.03 (s, 3H). LCMS (M+H)=457.4. And (S)-ethyl 2-(5-bromo-4-(4,4-dimethylpiperidin-1-yl)-2,6-dimethylpyridin-3-yl)-2-hydroxyacetate (0.3 g, 0.751 mmol, 12.24% yield) as pale yellow paste: LCMS (M+H)=401.3.

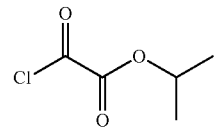

The propan-2-ol (38.2 mL, 499 mmol) was added drop wise over 15 min to a cold (0° C.), nitrogen purged solution of oxalyl dichloride (101 g, 799 mmol) and the reaction was stirred at room temperature for 2.5 h. Then a reflux condenser was fitted and a slight vacuum was applied for about 1 h until HCl gas was removed (the HCl was trapped in by a sat'd solution of $NaHCO_3$). The reflux condenser was removed and the flask was fitted with a short path distillation head. Excess reagent was removed by distillation under house vacuum (oil bath heated to 65° C.), and then the temperature was raised to between 85-95° C. and the product was distilled (NOTE: The $1^{st}$ fraction of ~5 mL was discarded) to provide isopropyl 2-chloro-2-oxoacetate 52.62 g (70%).

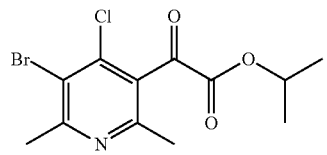

A solution of 2M isopropyl magnesium chloride (84 mL, 168 mmol) was added drop wise over 20 min to a cold (−70° C.), nitrogen purged solution of 3,5-dibromo-4-chloro-2,6-dimethylpyridine (48 g, 160 mmol) and copper(I)bromide-dimethyl sulfide complex (1.65 g, 8.02 mmol) in THF (240 mL), which was then allowed to warm to −10° C. over 60 min. The reaction mixture was transferred via cannula into a 1 L RB-flask containing isopropyl 2-chloro-2-oxoacetate (26.6 g, 176 mmol) in THF (160 mL) maintained at −60° C., and the reaction stirred an additional 2.5 h while being allowed to warm to −10° C. The reaction was quenched upon diluted with a mixture of 10% $NH_4Cl$ solution (80 mL) in ether (320 mL). The organic layer was washed with 160 mL of sat'd $NaHCO_3$/10% $NH_4Cl$ solution (1:1), brine, and dried ($Na_2SO_4$). The crude product was charged (DCM solution) to a 330 g ISCO silica gel cartridge and gradient eluted (5-20% EtOAc/hexanes) using an Isolera chromatography station gave isopropyl 2-(5-bromo-4-chloro-2,6-dimethylpyridin-3-yl)-2-oxoacetate 40.38 g (76%). ¹H NMR (500 MHz, CDCl₃) δ 5.28-5.21 (m, 1H), 2.77 (s, 3H), 2.47 (s, 3H), 1.40 (d, J=6.3 Hz, 6H). LCMS (M+H)=336.04.

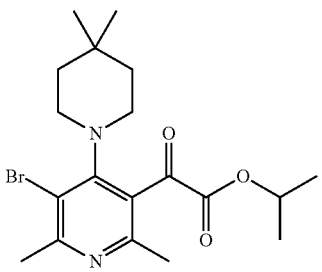 [SMILES: Cc1nc(C)c(C(=O)C(=O)OC(C)C)c(N2CCC(C)(C)CC2)c1Br]

To a stirred solution of isopropyl 2-(5-bromo-4-chloro-2,6-dimethylpyridin-3-yl)-2-oxoacetate (7.2 g, 21.52 mmol) and DIEA (4.13 mL, 23.67 mmol) in anhydrous acetonitrile (15 mL) was added 4,4-dimethylpiperidine (2.68 g, 23.67 mmol) in acetonitrile (15 mL). The resulting solution was placed in a pre-heated oil bath at 75° C. After heating (75-78° C.) for 24 h and the temperature was raised to 85° C. for 24 h. Another portion of DIEA (3.5 mL, 20.04 mmol) and 4,4-dimethylpiperidine (0.27 g, 2.4 mmol) in acetonitrile (3 mL) was added and hearted at 85° C. for a day. The reaction mixture was diluted with ether (100 mL), washed with water (100 mL), brine (50 mL), dried (MgSO₄), filtered, concentrated and purified by ISCO 120 g cartridge (EtOAc/hex: 0 to 20%) to afford isopropyl 2-(5-bromo-4-(4,4-dimethylpiperidin-1-yl)-2,6-dimethylpyridin-3-yl)-2-oxoacetate (6.8 g, 16.53 mmol, 77% yield. ¹H NMR (500 MHz, CDCl₃) δ 5.25-5.11 (m, 1H), 3.17 (br. s., 4H), 2.71 (s, 3H), 2.41 (s, 3H), 1.42-1.37 (m, 10H), 1.00 (s, 6H).). LCMS (M+H)=413.3.

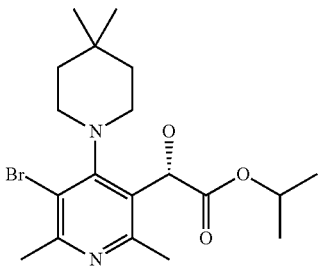 [SMILES: Cc1nc(C)c([C@H](O)C(=O)OC(C)C)c(N2CCC(C)(C)CC2)c1Br]

To a yellow solution of isopropyl 2-(5-bromo-4-(4,4-dimethylpiperidin-1-yl)-2,6-dimethylpyridin-3-yl)-2-oxoacetate (7.7 g, 18.72 mmol) and (R)-1-methyl-3,3-diphenylhexahydropyrrolo[1,2-c][1,3,2]oxazaborole (7.5 mL, 7.50 mmol) in anhydrous toluene (100 mL) was added drop wise 50% catecholborane/toluene (6 mL, 28.0 mmol) over 5 min at −50° C. Then, the reaction mixture was slowly warmed to −30° C. over 1 h and left in refrigerator (−20° C.) for 3 days. Then, the reaction mixture was diluted with EtOAc (100 mL) and 20 mL of 1M Na₂CO₃, and vigorously stirred for 30 min. Aqueous layer separated and organic layer washed with sat'd Na₂CO₃ (2×25 mL) by vigorously stirring for 15 each time, then dried (MgSO₄), filtered and concentrated to give crude product as light purple paste which was purified by flash chromatography using 0 to 40% EtOAc/hex to afford (S)-isopropyl 2-(5-bromo-4-(4,4-dimethylpiperidin-1-yl)-2,6-dimethylpyridin-3-yl)-2-hydroxyacetate (6.7 g, 15.72 mmol, 84% yield) as colorless thick paste. ¹H NMR (500 MHz, CDCl₃) δ 5.85 (d, J=5.7 Hz, 1H), 5.59 (d, J=7.4 Hz, 1H), 5.08 (dt, J=12.5, 6.3 Hz, 1H), 3.98-3.88 (m, 1H), 3.88-3.78 (m, 1H), 2.76-2.68 (m, 1H), 2.67 (s, 3H), 2.64-2.58 (m, 1H), 2.57 (s, 3H), 1.73 (td, J=12.8, 4.8 Hz, 1H), 1.65-1.59 (m, 1H), 1.47-1.35 (m, 2H), 1.27 (d, J=6.3 Hz, 3H), 1.17 (d, J=6.1 Hz, 3H), 1.09 (s, 3H), 1.04 (s, 3H). LCMS (M+H)=414.6.

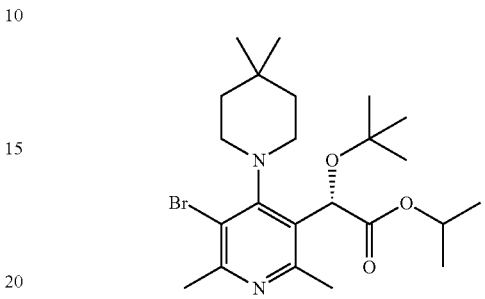

A stirred ice-cold yellow mixture of (S)-isopropyl 2-(5-bromo-4-(4,4-dimethylpiperidin-1-yl)-2,6-dimethylpyridin-3-yl)-2-hydroxyacetate (6.7 g, 16.21 mmol) and 70% HClO₄ (2.2 mL, 25.6 mmol) in dichloromethane (400 mL) was saturated with isobutylene gas by bubbling through the reaction mixture (10 min). The reaction mixture was cloudy sealed in a seal tube, stirred for 24 h at rt. The reaction mixture was recooled in a −10° C. bath, bubbled additional isobutylene (~15 min). The reaction mixture became a clear solution at this point. The tube was sealed and stirred at rt for 16 h. LCMs at this point showed incomplete reaction. So, the reaction mixture was cooled down to −30° C. and bubbled isobutene (~15 min). After 24 h, reaction mixture was neutralized with sat. Na₂CO₃ (20 mL), organic layer separated and aqueous layer was extracted with CH₂Cl₂ (25 mL). The combined organic layers were dried (MgSO₄), filtered, concentrated and purified on a ISCO 120 g column (EtOAc/hex: 0 to 40%) to afford (S)-isopropyl 2-(5-bromo-4-(4,4-dimethylpiperidin-1-yl)-2,6-dimethylpyridin-3-yl)-2-(tert-butoxy)acetate (5.43 g, 9.83 mmol, 60.7% yield) as a viscous oil. ¹H NMR (500 MHz, CDCl₃) δ 6.26 (br. s., 1H), 5.09-4.97 (m, 1H), 4.06 (br. s., 1H), 3.51 (br. s., 1H), 2.90 (br. s., 1H), 2.65 (s, 3H), 2.56 (s, 3H), 1.72-1.54 (m, 3H), 1.47 (br. s., 1H), 1.37 (br. s., 1H), 1.23-1.20 (m, 12H), 1.15 (d, J=6.1 Hz, 3H), 1.09 (br. s., 3H), 1.04 (br. s., 3H). LCMS (M+H)=471.3.

Preparation of Intermediates (S)-ethyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate and (S)-2-(tert-butoxy)-2-(4-(4,4-dimethylpiperidin-1-yl)-2,6-dimethyl-5-(1,2,3,4-tetrahydroisoquinolin-6-yl)pyridin-3-yl)acetic acid from (S)-ethyl 2-(5-bromo-4-(4,4-dimethylpiperidin-1-yl)-2,6-dimethylpyridin-3-yl)-2-(tert-butoxy)acetate

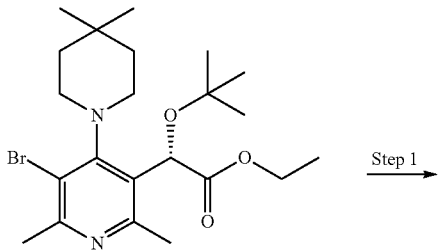

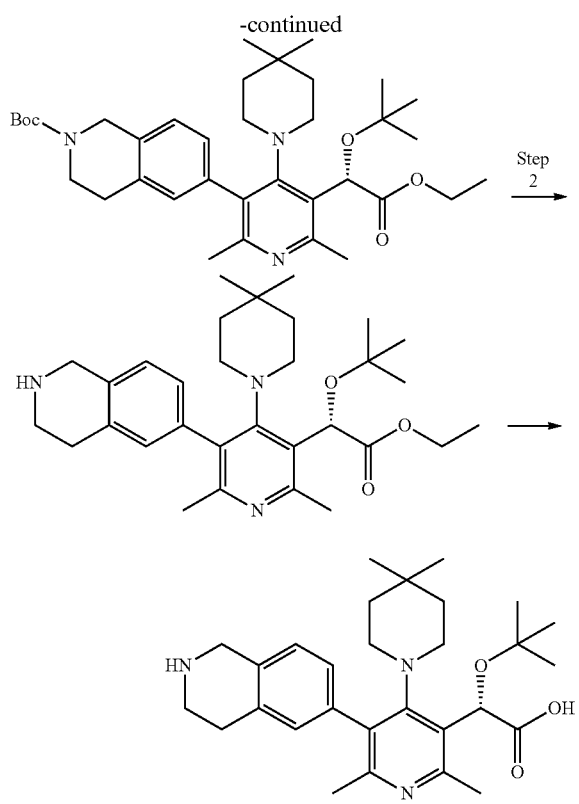

Step 1: To a mixture of (S)-ethyl 2-(5-bromo-4-(4,4-dimethylpiperidin-1-yl)-2,6-dimethylpyridin-3-yl)-2-(tert-butoxy)acetate (500 mg), (2-(tert-butoxycarbonyl)-1,2,3,4-tetrahydroisoquinolin-6-yl)boronic acid (365 mg) and Cs$_2$CO$_3$ (715 mg) in 1,4-dioxane (25 mL) and water (5 mL) was added Pd(PPh$_3$)$_4$ (127 mg). The mixture was flushed with nitrogen and then heated at 85° C. for 3 hours. The mixture was diluted with water (20 mL) and then extracted with EtOAc (2×20 mL). The organic layers were combined, washed with brine and concentrated under vacuum to give a crude of (S)-tert-butyl 6-(5-(1-(tert-butoxy)-2-ethoxy-2-oxoethyl)-4-(4,4-dimethylpiperidin-1-yl)-2,6-dimethylpyridin-3-yl)-3,4-dihydroisoquinoline-2(1H)-carboxylate which was used as is. LCMS (M+H)$^+$: 608.5.

Step 2: To a solution of (S)-tert-butyl 6-(5-(1-(tert-butoxy)-2-ethoxy-2-oxoethyl)-4-(4,4-dimethylpiperidin-1-yl)-2,6-dimethylpyridin-3-yl)-3,4-dihydroisoquinoline-2(1H)-carboxylate (200 mg) in CH$_2$Cl$_2$ (20 mL) was added TFA (1 mL). The reaction was stirred at room temperature for 3 hours. All the solvents were removed under vacuum to give rude (S)-ethyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate which was used without further purification. LCMS (M+H)$^+$: 508.3.

Step 3: To a solution of (S)-ethyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate (10 mg) in MeOH (1 mL) and THF (1 mL) was added sodium hydroxide (0.158 mL, 1N). The reaction was stirred at 80° C. for 2 hours. The mixture was acidified by 1N HCl to pH ~4. All the solvents was removed under vacuum to give a residue which was purified by preparative HPLC system. LCMS (M+H)$^+$: 480.3.

Preparation of Intermediates (S)-isopropyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate and (S)-2-(tert-butoxy)-2-(4-(4,4-dimethylpiperidin-1-yl)-2,6-dimethyl-5-(1,2,3,4-tetrahydroisoquinolin-6-yl)pyridin-3-yl)acetic acid from (S)-isopropyl 2-(5-bromo-4-(4,4-dimethylpiperidin-1-yl)-2,6-dimethylpyridin-3-yl)-2-(tert-butoxy)acetate

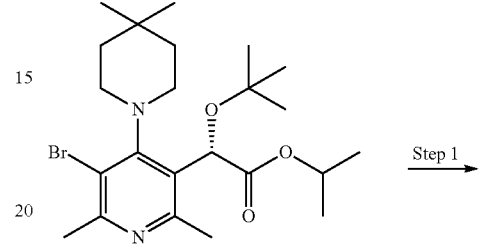

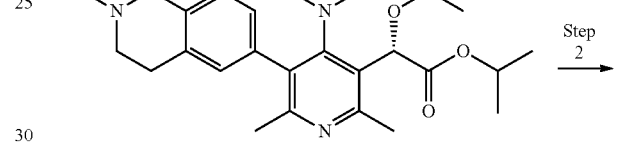

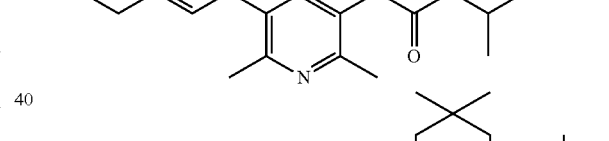

Step 1: To a mixture of (S)-isopropyl 2-(5-bromo-4-(4,4-dimethylpiperidin-1-yl)-2,6-dimethylpyridin-3-yl)-2-(tert-butoxy)acetate (1.1 g), (2-(tert-butoxycarbonyl)-1,2,3,4-tetrahydroisoquinolin-6-yl)boronic acid (0.649 g) and Cs$_2$CO$_3$ (1.527 g) in 1,4-dioxane (40 mL) and water (8 mL) was added Pd(PPh$_3$)$_4$ (0.271 g). The mixture was flushed with nitrogen and then heated at 85° C. for 5 hours. The mixture was diluted with water (50 mL) and then extracted with EtOAc (2×50 mL). The organic layers were combined, washed with brine and concentrated under vacuum to give a residue which was purified by silica gel chromatography (hexane/EtOAc=10:1 to 3:1) to give (S)-tert-butyl 6-(5-(1-(tert-butoxy)-2-isopropoxy-2-oxoethyl)-4-(4,4-dimethylpiperidin-1-yl)-2,6-dimethylpyridin-3-yl)-3,4-dihydroisoquinoline-2(1H)-carboxylate. LCMS (M+H)$^+$: 622.4.

Step 2: To a solution of (S)-tert-butyl 6-(5-(1-(tert-butoxy)-2-isopropoxy-2-oxoethyl)-4-(4,4-dimethylpiperidin- 1-yl)-2,6-dimethylpyridin-3-yl)-3,4-dihydroisoquinoline-2 (1H)-carboxylate (420 mg) in CH$_2$Cl$_2$ (5 mL) was added TFA (1 mL). The reaction mixture was stirred at room temperature for 4 hours. All the solvents were removed under vacuum to give (S)-isopropyl 2-(tert-butoxy)-2-(4-(4, 4-dimethylpiperidin-1-yl)-2,6-dimethyl-5-(1,2,3,4-tetrahydroisoquinolin-6-yl)pyridin-3-yl)acetate which was used without further purification. LCMS (M+H)$^+$: 522.3.

Step 3: To a solution of (S)-isopropyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate (50 mg) in ethanol (4 mL) was added KOH (43.0 mg) and water (0.4 mL). The reaction mixture was heated at 85° C. for 6 hours. The mixture was acidified by 1N HCl to pH=4. All the solvents were removed under vacuum. The residue was used without further purification. LCMS (M+H)$^+$: 480.2.

General Procedure A for the Preparation of Claim I, from (S)-ethyl or (S)-isopropyl 2-(tert-butoxy)-2-(4-(4,4-dimethylpiperidin-1-yl)-2,6-dimethyl-5-(1,2, 3,4-tetrahydroisoquinolin-6-yl)pyridin-3-yl)acetate etate (1 eq.) and an electrophile (1-20 eq.) in acetonitrile or THF or DMF or dioxane. The reaction was carried out at room temperature or at an increased temperature (up to 150° C.) for a period of time (10 minutes to 72 hours). After removal of solvents under vacuum, the residue was used as is or purified by the preparative HPLC system.

Step 2: To a solution of the product from the step 1 (1 eq.) in MeOH or EtOH and THF 5 (volume ratio 20:1 to 1:20) was added NaOH or KOH (1 to 100 eq.). The reaction was carried out at room temperature or at an increased temperature (up to 150° C.) for a period of time (10 minutes to 72 hours). The mixture was acidified by 1N HCl to pH ~4. Removal of the solvents under vacuum gave a residue which was purified by the preparative HPLC system to provide desired product.

General Procedure B for the Preparation of Claim I, from (S)-2-(tert-butoxy)-2-(4-(4,4-dimethylpiperidin-1-yl)-2,6-dimethyl-5-(1,2,3,4-tetrahydroisoquinolin-6-yl)pyridin-3-yl)acetic acid

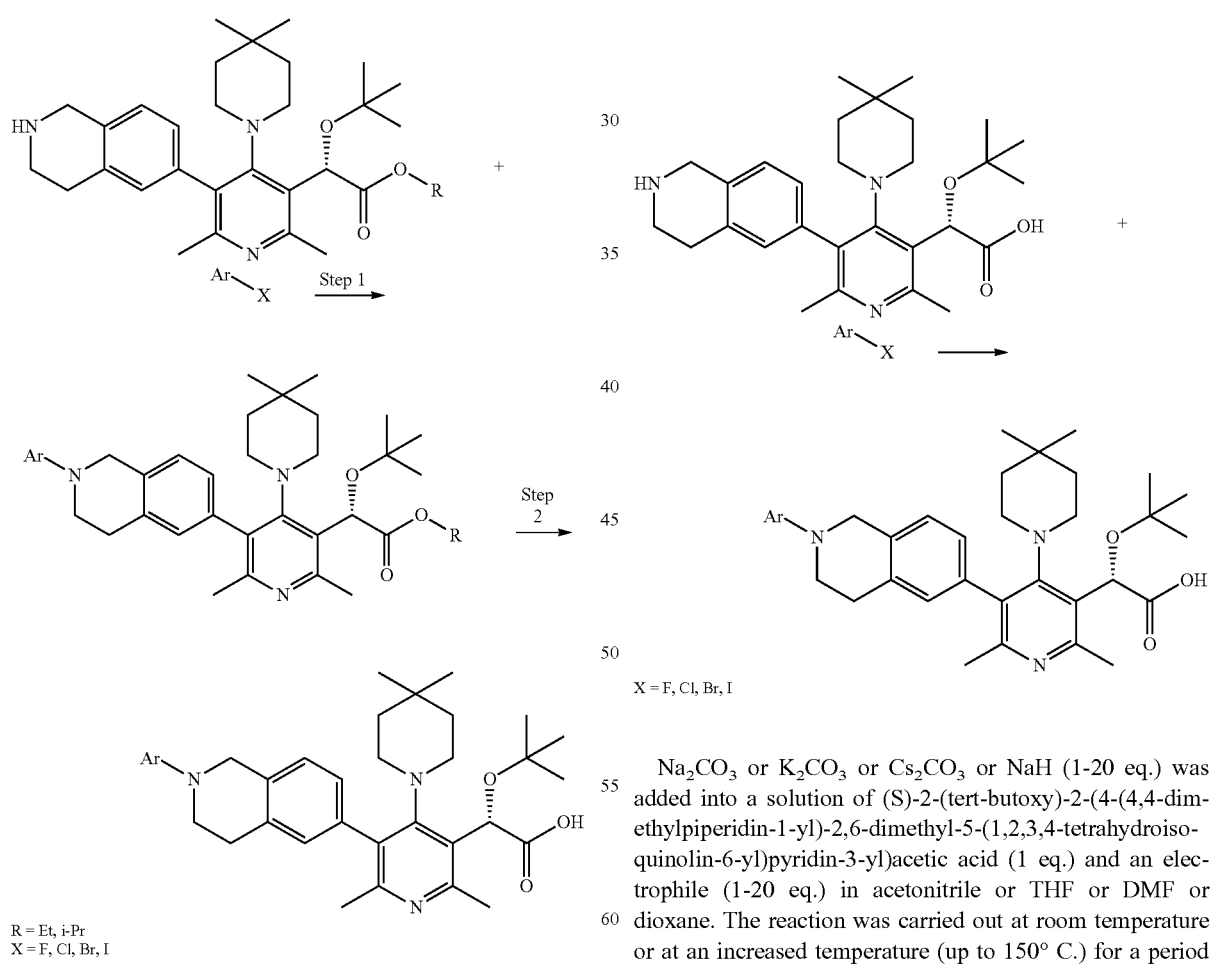

R = Et, i-Pr
X = F, Cl, Br, I

Step 1: Na$_2$CO$_3$ or K$_2$CO$_3$ or Cs$_2$CO$_3$ or NaH (1-20 eq.) was added into a solution of (S)-Ethyl of (S)-isopropyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)ac- X = F, Cl, Br, I Na$_2$CO$_3$ or K$_2$CO$_3$ or Cs$_2$CO$_3$ or NaH (1-20 eq.) was added into a solution of (S)-2-(tert-butoxy)-2-(4-(4,4-dimethylpiperidin-1-yl)-2,6-dimethyl-5-(1,2,3,4-tetrahydroisoquinolin-6-yl)pyridin-3-yl)acetic acid (1 eq.) and an electrophile (1-20 eq.) in acetonitrile or THF or DMF or dioxane. The reaction was carried out at room temperature or at an increased temperature (up to 150° C.) for a period of time (10 minutes to 72 hours). The mixture was diluted with EtOAc, washed with water, and dried over MgSO$_4$. After removal of solvents under vacuum, the residue was purified by the preparative HPLC system to afford desired product.

| Method | Name | Structure | LCMS (M + H)+ |
|---|---|---|---|
| A | (S)-2-(tert-butoxy)-2-(4-(4,4-dimethylpiperidin-1-yl)-2,6-dimethyl-5-(2-(6-(trifluoromethyl)thiazolo[4,5-b]pyridin-2-yl)-1,2,3,4-tetrahydroisoquinolin-6-yl)pyridin-3-yl)acetic acid | 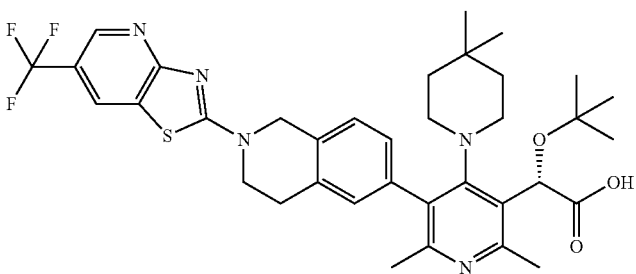 [SMILES: Cc1nc(C)c([C@H](OC(C)(C)C)C(=O)O)c(N2CCC(C)(C)CC2)c1-c1ccc2c(c1)CCN(c1nc3ncc(C(F)(F)F)cc3s1)C2]  1 | 682.2 |
| A | (S)-2-(tert-butoxy)-2-(4-(4,4-dimethylpiperidin-1-yl)-2,6-dimethyl-5-(2-(thiazolo[5,4-b]pyridin-2-yl)-1,2,3,4-tetrahydroisoquinolin-6-yl)pyridin-3-yl)acetic acid | 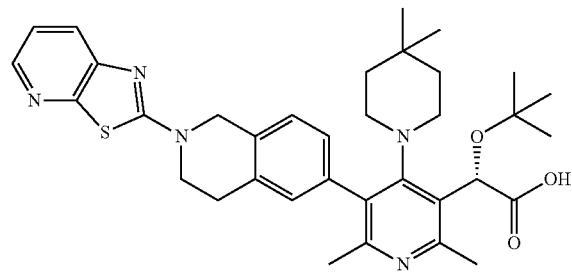 [SMILES: Cc1nc(C)c([C@H](OC(C)(C)C)C(=O)O)c(N2CCC(C)(C)CC2)c1-c1ccc2c(c1)CCN(c1nc3cccnc3s1)C2]  2 | 614.2 |
| A | (S)-2-(tert-butoxy)-2-(5-(2-(7-chlorothiazolo[5,4-c]pyridin-2-yl)-1,2,3,4-tetrahydroisoquinolin-6-yl)-4-(4,4-dimethylpiperidin-1-yl)-2,6-dimethylpyridin-3-yl)acetic acid | 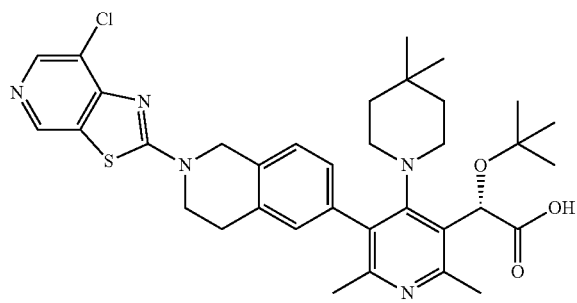 [SMILES: Cc1nc(C)c([C@H](OC(C)(C)C)C(=O)O)c(N2CCC(C)(C)CC2)c1-c1ccc2c(c1)CCN(c1nc3c(Cl)cncc3s1)C2]  3 | 648.2 |

-continued

| Method | Name | Structure | LCMS (M + H)+ |
|---|---|---|---|
| A | (S)-2-(tert-butoxy)-2-(5-(2-(6-chlorobenzo[d]thiazol-2-yl)-1,2,3,4-tetrahydroisoquinolin-6-yl)-4-(4,4-dimethylpiperidin-1-yl)-2,6-dimethylpyridin-3-yl)acetic acid | 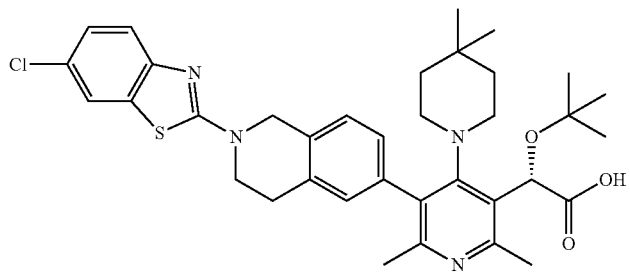 [SMILES: Cc1nc(C)c([C@H](OC(C)(C)C)C(=O)O)c(N2CCC(C)(C)CC2)c1-c1ccc2c(c1)CCN(c1nc3ccc(Cl)cc3s1)C2] 4 | 647.2 |
| A | (S)-2-(tert-butoxy)-2-(5-(2-(5,6-dichlorobenzo[d]thiazol-2-yl)-1,2,3,4-tetrahydroisoquinolin-6-yl)-4-(4,4-dimethylpiperidin-1-yl)-2,6-dimethylpyridin-3-yl)acetic acid | 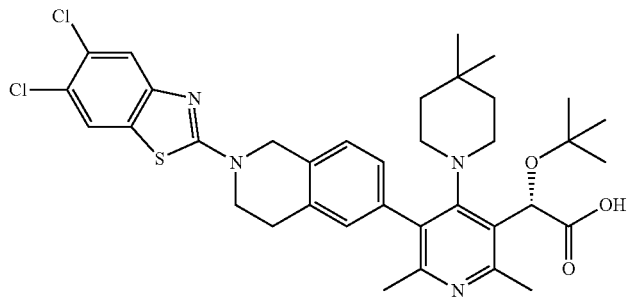 [SMILES: Cc1nc(C)c([C@H](OC(C)(C)C)C(=O)O)c(N2CCC(C)(C)CC2)c1-c1ccc2c(c1)CCN(c1nc3cc(Cl)c(Cl)cc3s1)C2] 5 | 681.1 |
| A | (S)-2-(tert-butoxy)-2-(4-(4,4-dimethylpiperidin-1-yl)-2,6-dimethyl-5-(2-(5-methylbenzo[d]thiazol-2-yl)-1,2,3,4-tetrahydroisoquinolin-6-yl)pyridin-3-yl)acetic acid | 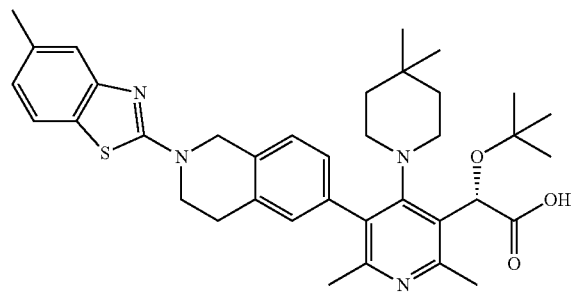 [SMILES: Cc1ccc2sc(N3CCc4cc(-c5c(C)nc(C)c([C@H](OC(C)(C)C)C(=O)O)c5N5CCC(C)(C)CC5)ccc4C3)nc2c1] 6 | 627.3 |

| Method | Name | Structure | LCMS (M + H)⁺ |
|---|---|---|---|
| A | (S)-2-(tert-butoxy)-2-(5-(2-(4-chlorobenzo[d]thiazol-2-yl)-1,2,3,4-tetrahydroisoquinolin-6-yl)-4-(4,4-dimethylpiperidin-1-yl)-2,6-dimethylpyridin-3-yl)acetic acid | 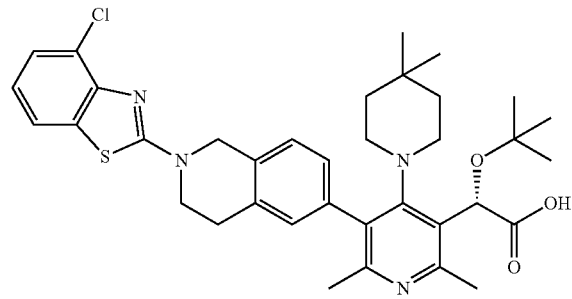 [SMILES: Cc1nc(C)c([C@H](OC(C)(C)C)C(=O)O)c(N2CCC(C)(C)CC2)c1-c1ccc2c(c1)CCN(c1nc3c(Cl)cccc3s1)C2] 7 | 647.3 |
| A | (S)-2-(tert-butoxy)-2-(4-(4,4-dimethylpiperidin-1-yl)-5-(2-(6-fluorobenzo[d]thiazol-2-yl)-1,2,3,4-tetrahydroisoquinolin-6-yl)-2,6-dimethylpyridin-3-yl)acetic acid | 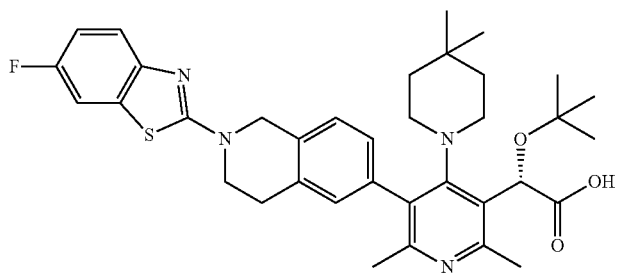 [SMILES: Cc1nc(C)c([C@H](OC(C)(C)C)C(=O)O)c(N2CCC(C)(C)CC2)c1-c1ccc2c(c1)CCN(c1nc3ccc(F)cc3s1)C2] 8 | 631.3 |
| A | (S)-2-(tert-butoxy)-2-(4-(4,4-dimethylpiperidin-1-yl)-2,6-dimethyl-5-(2-(6-methylbenzo[d]thiazol-2-yl)-1,2,3,4-tetrahydroisoquinolin-6-yl)pyridin-3-yl)acetic acid | 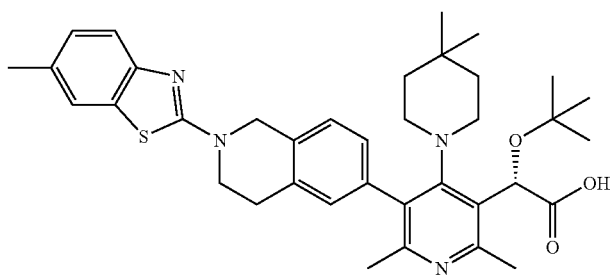 [SMILES: Cc1ccc2nc(N3CCc4cc(-c5c(C)nc(C)c([C@H](OC(C)(C)C)C(=O)O)c5N5CCC(C)(C)CC5)ccc4C3)sc2c1] 9 | 627.3 |

-continued

| Method | Name | Structure | LCMS (M + H)+ |
|---|---|---|---|
| A | (S)-2-(tert-butoxy)-2-(4-(4,4-dimethylpiperidin-1-yl)-2,6-dimethyl-5-(2-(thiazolo[4,5-b]pyridin-2-yl)-1,2,3,4-tetrahydroisoquinolin-6-yl)pyridin-3-yl)acetic acid | 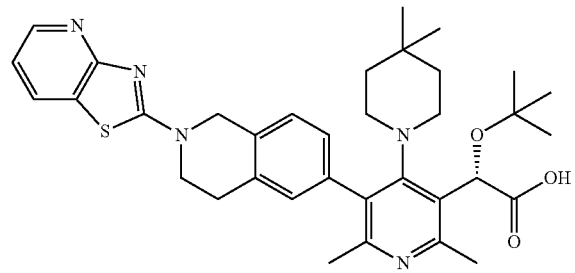 [SMILES: Cc1nc(C)c([C@H](OC(C)(C)C)C(=O)O)c(N2CCC(C)(C)CC2)c1-c1ccc2c(c1)CCN(c1nc3ncccc3s1)C2]<br>10 | 614.3 |
| A | (S)-2-(tert-butoxy)-2-(4-(4,4-dimethylpiperidin-1-yl)-2,6-dimethyl-5-(2-(thiazolo[4,5-c]pyridin-2-yl)-1,2,3,4-tetrahydroisoquinolin-6-yl)pyridin-3-yl)acetic acid | 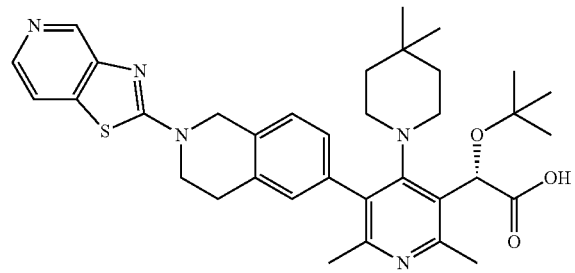 [SMILES: Cc1nc(C)c([C@H](OC(C)(C)C)C(=O)O)c(N2CCC(C)(C)CC2)c1-c1ccc2c(c1)CCN(c1nc3cnccc3s1)C2]<br>11 | 614.1 |
| A | (S)-2-(tert-butoxy)-2-(4-(4,4-dimethylpiperidin-1-yl)-5-(2-(6-methoxybenzo[d]thiazol-2-yl)-1,2,3,4-tetrahydroisoquinolin-6-yl)-2,6-dimethylpyridin-3-yl)acetic acid | 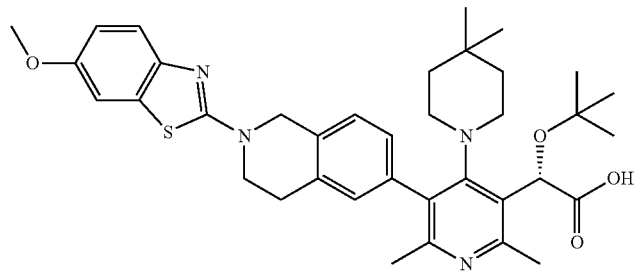 [SMILES: COc1ccc2nc(N3CCc4cc(-c5c(C)nc(C)c([C@H](OC(C)(C)C)C(=O)O)c5N5CCC(C)(C)CC5)ccc4C3)sc2c1]<br>12 | 643.3 |

| Method | Name | Structure | LCMS (M + H)+ |
|---|---|---|---|
| A | (S)-2-(5-(2-(benzo[d]thiazol-2-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid | 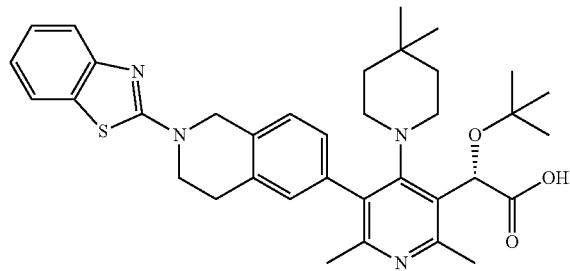 [SMILES: Cc1nc(C)c([C@H](OC(C)(C)C)C(=O)O)c(N2CCC(C)(C)CC2)c1-c1ccc2c(c1)CCN(c1nc3ccccc3s1)C2]<br>13 | 613.3 |
| A | (S)-2-(tert-butoxy)-2-(4-(4,4-dimethylpiperidin-1-yl)-2,6-dimethyl-5-(2-(thieno[2,3-d]pyrimidin-4-yl)-1,2,3,4-tetrahydroisoquinolin-6-yl)pyridin-3-yl)acetic acid | 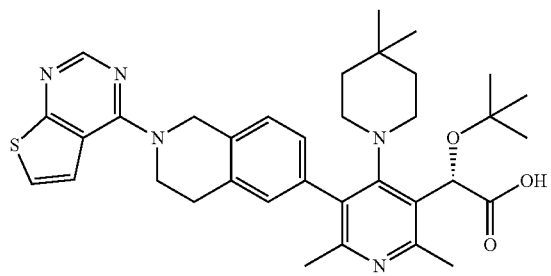 [SMILES: Cc1nc(C)c([C@H](OC(C)(C)C)C(=O)O)c(N2CCC(C)(C)CC2)c1-c1ccc2c(c1)CCN(c1ncnc3sccc13)C2]<br>14 | 614.3 |
| A | (S)-2-(tert-butoxy)-2-(4-(4,4-dimethylpiperidin-1-yl)-2,6-dimethyl-5-(2-(7-methylthieno[3,2-d]pyrimidin-4-yl)-1,2,3,4-tetrahydroisoquinolin-6-yl)pyridin-3-yl)acetic acid | 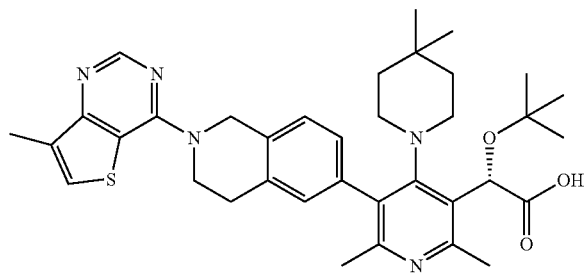 [SMILES: Cc1nc(C)c([C@H](OC(C)(C)C)C(=O)O)c(N2CCC(C)(C)CC2)c1-c1ccc2c(c1)CCN(c1ncnc3c(C)csc13)C2]<br>15 | 628.3 |

| Method | Name | Structure | LCMS (M + H)⁺ |
|---|---|---|---|
| A | (S)-2-(tert-butoxy)-2-(4-(4,4-dimethylpiperidin-1-yl)-2,6-dimethyl-5-(2-(1-methyl-1H-pyrazolo[3,4-d]pyrimidin-4-yl)-1,2,3,4-tetrahydroisoquinolin-6-yl)pyridin-3-yl)acetic acid | 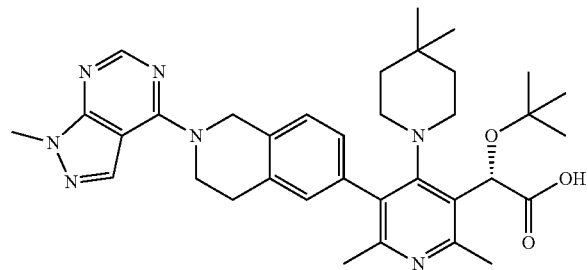 [SMILES: Cc1nc(C)c([C@H](OC(C)(C)C)C(=O)O)c(N2CCC(C)(C)CC2)c1-c1ccc2c(c1)CCN(c1ncnc3c1cnn3C)C2] 16 | 612.3 |
| B | (S)-2-(tert-butoxy)-2-(4-(4,4-dimethylpiperidin-1-yl)-2,6-dimethyl-5-(2-(1-methyl-1H-benzo[d]imidazol-2-yl)-1,2,3,4-tetrahydroisoquinolin-6-yl)pyridin-3-yl)acetic acid | 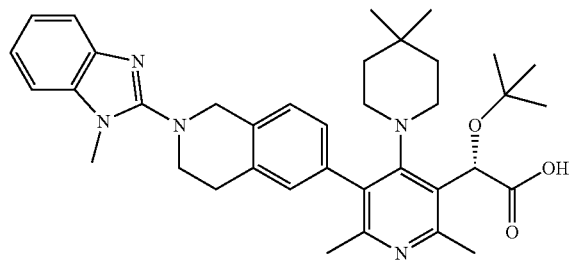 [SMILES: Cc1nc(C)c([C@H](OC(C)(C)C)C(=O)O)c(N2CCC(C)(C)CC2)c1-c1ccc2c(c1)CCN(c1nc3ccccc3n1C)C2] 17 | 610.2 |
| B | (S)-2-(5-(2-(benzo[d]isoxazol-3-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid | 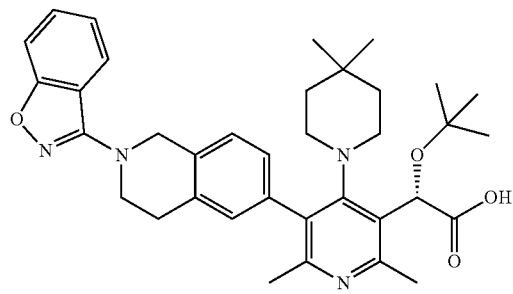 [SMILES: Cc1nc(C)c([C@H](OC(C)(C)C)C(=O)O)c(N2CCC(C)(C)CC2)c1-c1ccc2c(c1)CCN(c1noc3ccccc13)C2] 18 | 597.2 |

| Method | Name | Structure | LCMS (M + H)+ |
|---|---|---|---|
| B | (S)-2-(tert-butoxy)-2-(5-(2-(1,6-dimethyl-1H-pyrazolo[3,4-d]pyrimidin-4-yl)-1,2,3,4-tetrahydroisoquinolin-6-yl)-4-(4,4-dimethylpiperidin-1-yl)-2,6-dimethylpyridin-3-yl)acetic acid 19 | | 626.3 |
| B | (S)-2-(5-(2-(7H-pyrrolo[2,3-d]pyrimidin-4-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid 20 | | 597.3 |
| B | (S)-2-(tert-butoxy)-2-(4-(4,4-dimethylpiperidin-1-yl)-5-(2-(6-hydroxy-7H-purin-2-yl)-1,2,3,4-tetrahydroisoquinolin-6-yl)-2,6-dimethylpyridin-3-yl)acetic acid 21 | | 614.2 |
| B | (S)-2-(5-(2-(5H-pyrrolo[3,2-d]pyrimidin-4-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid 22 | | 597.2 |

| Method | Name | Structure | LCMS (M + H)+ |
|---|---|---|---|
| B | (S)-2-(tert-butoxy)-2-(4-(4,4-dimethylpiperidin-1-yl)-2,6-dimethyl-5-(2-(6-(methylamino)-7H-purin-2-yl)-1,2,3,4-tetrahydroisoquinolin-6-yl)pyridin-3-yl)acetic acid | 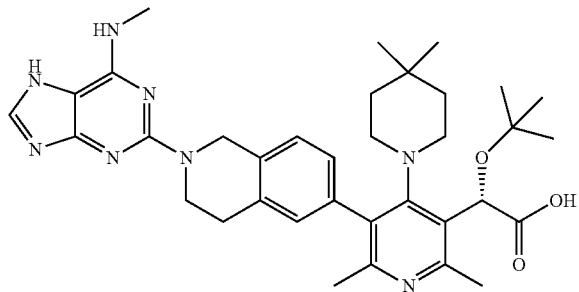 [SMILES: CNc1nc(N2CCc3cc(-c4c(C)nc(C)c([C@H](OC(C)(C)C)C(=O)O)c4N4CCC(C)(C)CC4)ccc3C2)nc2nc[nH]c12] 23 | 627.3 |
| B | (S)-2-(5-(2-(1H-imidazo[4,5-c]pyridin-4-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid | 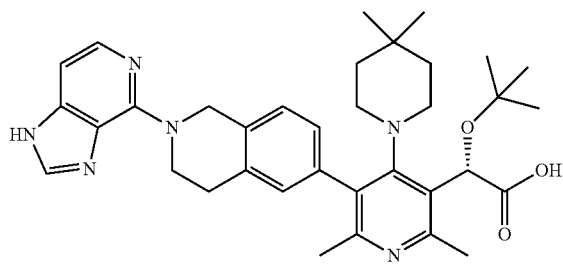 [SMILES: Cc1nc(C)c([C@H](OC(C)(C)C)C(=O)O)c(N2CCC(C)(C)CC2)c1-c1ccc2c(c1)CCN(c1nccc3[nH]cnc13)C2] 24 | 597.3 |
| B | (S)-2-(5-(2-(7H-pyrrolo[2,3-d]pyrimidin-2-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid | 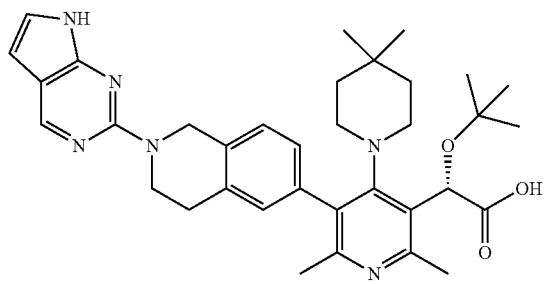 [SMILES: Cc1nc(C)c([C@H](OC(C)(C)C)C(=O)O)c(N2CCC(C)(C)CC2)c1-c1ccc2c(c1)CCN(c1ncc3cc[nH]c3n1)C2] 25 | 597.3 |

| Method | Name | Structure | LCMS (M + H)+ |
|---|---|---|---|
| B | (S)-2-(5-(2-(7H-purin-6-yl)-1,2,3,4-tetrahydroisoquinolin-6-yl)-4-(4,4-dimethylpiperidin-1-yl)-2,6-dimethylpyridin-3-yl)-2-(tert-butoxy)acetic acid | 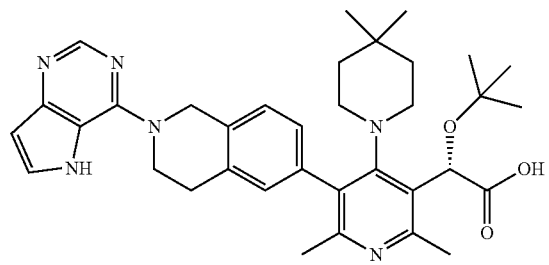 [SMILES: Cc1nc(C)c([C@H](OC(C)(C)C)C(=O)O)c(N2CCC(C)(C)CC2)c1-c1ccc2c(c1)CCN(c1ncnc3cc[nH]c13)C2]<br>26 | 598.1 |
| B | (S)-2-(tert-butoxy)-2-(4-(4,4-dimethylpiperidin-1-yl)-5-(2-(2-methoxy-7H-pyrrolo[2,3-d]pyrimidin-4-yl)-1,2,3,4-tetrahydroisoquinolin-6-yl)-2,6-dimethylpyridin-3-yl)acetic acid | 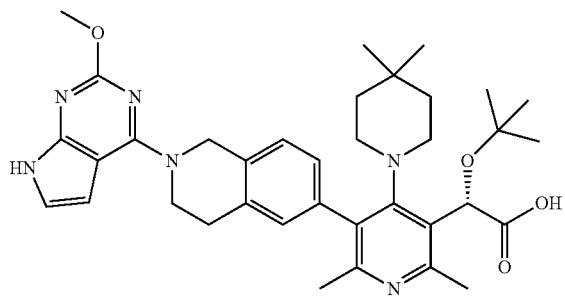 [SMILES: COc1nc(N2CCc3cc(-c4c(C)nc(C)c([C@H](OC(C)(C)C)C(=O)O)c4N4CCC(C)(C)CC4)ccc3C2)c2cc[nH]c2n1]<br>27 | 627.2 |
| B | (S)-2-(tert-butoxy)-2-(5-(2-(6-(tert-butyl)thieno[3,2-d]pyrimidin-4-yl)-1,2,3,4-tetrahydroisoquinolin-6-yl)-4-(4,4-dimethylpiperidin-1-yl)-2,6-dimethylpyridin-3-yl)acetic acid | 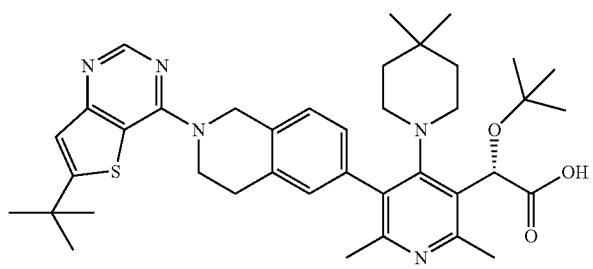 [SMILES: Cc1nc(C)c([C@H](OC(C)(C)C)C(=O)O)c(N2CCC(C)(C)CC2)c1-c1ccc2c(c1)CCN(c1ncnc3cc(C(C)(C)C)sc13)C2]<br>28 | 670.3 |

| Method | Name | Structure | LCMS (M + H)+ |
|---|---|---|---|
| B | (S)-2-(tert-butoxy)-2-(5-(2-(5-chlorobenzo[d]oxazol-2-yl)-1,2,3,4-tetrahydroisoquinolin-6-yl)-4-(4,4-dimethylpiperidin-1-yl)-2,6-dimethylpyridin-3-yl)acetic acid | 29 | 631.2 |
| B | (S)-2-(tert-butoxy)-2-(4-(4,4-dimethylpiperidin-1-yl)-2,6-methyl-5-(2-(3-phenyl-3H-[1,2,3]triazolo[4,5-d]pyrimidin-7-yl)-1,2,3,4-tetrahydroisoquinolin-6-yl)pyridin-3-yl)acetic acid | 30 | 675.3 |

Biological Methods

Inhibition of HIV Replication:

A recombinant NL-RLuc proviral clone was constructed in which a section of the nef gene from NL4-3 was replaced with the Renilla Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC 18 at the PvuII site. The NL-RLuc virus was prepared by transfection of 293T cells with the plasmid pNLRLuc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). Results are shown in Table 1.

TABLE 1

| Compound | $EC_{50}$ μM |
|---|---|
| 1 | 0.003 |
| 2 | 0.001 |
| 3 | 0.001 |
| 4 | 0.019 |
| 5 | 0.012 |
| 6 | 0.022 |
| 7 | 0.002 |
| 8 | 0.005 |
| 9 | 0.008 |
| 10 | 0.002 |
| 11 | 0.001 |
| 12 | 0.004 |

TABLE 1-continued

| Compound | EC$_{50}$ μM |
|---|---|
| 13 | 0.007 |
| 14 | 0.002 |
| 15 | 0.002 |
| 16 | 0.002 |
| 17 | 0.022 |
| 18 | 0.005 |
| 19 | 0.001 |
| 20 | 0.003 |
| 21 | 5.986 |
| 22 | 0.286 |
| 23 | 0.062 |
| 24 | 0.056 |
| 25 | 0.004 |
| 26 | 0.02 |
| 27 | 0.002 |
| 28 | 0.013 |
| 29 | ND |
| 30 | ND |

ND = not determined

It will be evident to one skilled in the art that the present disclosure is not limited to the foregoing illustrative examples, and that it can be embodied in other specific forms 5 without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I

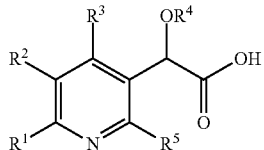

wherein:
$R^1$ is selected from hydrogen, alkyl, or cycloalkyl;
$R^2$ is tetrahydroisoquinolinyl and is substituted with 1 $R^6$ substituent and also with 0-3 halo or alkyl substituents;
$R^3$ is piperidinyl substituted with 0-3 substituents selected from cyano, halo, alkyl, haloalkyl, alkoxy, and haloalkoxy;
$R^4$ is selected from alkyl or haloalkyl;
$R^5$ is alkyl; and
$R^6$ is selected from benzothiazolyl, pyrazolopyrimidinyl, thiazolopyridinyl, triazolopymidinyl, benzooxazolyl, pyrrolopyrimidinyl, purinyl, imidazopyridinyl, benzoisoxazolyl, benzoimidazolyl or thienopyrimidinyl, and is substituted with 0-3 substituents selected from amino, cyano, halo, hydroxyl, alkyl, haloalkyl, alkoxy, and haloalkoxy;

or a pharmaceutically acceptable salt thereof.

2. A compound or salt of claim 1 wherein $R^2$ is tetrahydroisoquinolinyl substituted with 1 $R^6$ substituent.

3. A pharmaceutical composition comprising a compound or salt of claim 1.

* * * * *